United States Patent
Patek

(10) Patent No.: US 10,638,981 B2
(45) Date of Patent: May 5, 2020

(54) METHOD, SYSTEM AND COMPUTER READABLE MEDIUM FOR ASSESSING ACTIONABLE GLYCEMIC RISK

(71) Applicant: UNIVERSITY OF VIRGINIA PATENT FOUNDATION, Charlottesville, VA (US)

(72) Inventor: Stephen D Patek, Charlottesville, VA (US)

(73) Assignee: UNIVERSITY OF VIRGINIA PATENT FOUNDATION, Charlottesville, VA (US)

( * ) Notice: Subject to any disclaimer, the term of this patent is extended or adjusted under 35 U.S.C. 154(b) by 314 days.

(21) Appl. No.: 15/551,503

(22) PCT Filed: Feb. 16, 2016

(86) PCT No.: PCT/US2016/018027
§ 371 (c)(1),
(2) Date: Aug. 16, 2017

(87) PCT Pub. No.: WO2016/133879
PCT Pub. Date: Aug. 25, 2016

(65) Prior Publication Data
US 2018/0020988 A1      Jan. 25, 2018

Related U.S. Application Data

(60) Provisional application No. 62/116,791, filed on Feb. 16, 2015.

(51) Int. Cl.
*A61B 5/00* (2006.01)
*G16H 50/30* (2018.01)
(Continued)

(52) U.S. Cl.
CPC ........ *A61B 5/7275* (2013.01); *A61B 5/14532* (2013.01); *A61B 5/4839* (2013.01);
(Continued)

(58) Field of Classification Search
None
See application file for complete search history.

(56) References Cited

U.S. PATENT DOCUMENTS

2009/0171589 A1   7/2009  Kovatchev
2009/0240128 A1   9/2009  Mensinger et al.
(Continued)

FOREIGN PATENT DOCUMENTS

WO    WO 2014/022864 A1    2/2014

OTHER PUBLICATIONS

Patek et al.—Population-Specific Models of Glycemic Control in Intensive Care: Towards a Simulation-Based Methodology for Protocol Optimization; 2015 American Control Conference Palmer House Hilton Jul. 1-3, 2015. Chicago, IL, USA (Year: 2015).*
(Continued)

*Primary Examiner* — Kaylee R Wilson
*Assistant Examiner* — Jay B Shah
(74) *Attorney, Agent, or Firm* — Buchanan Ingersoll & Rooney PC

(57) ABSTRACT

A system, method and non-transient computer readable medium for assessing the opportunity to address either hyperglycemic or hypoglycemic risk (or both) in patients with diabetes based on historical continuous glucose monitoring (CGM) data.

17 Claims, 5 Drawing Sheets

(51) Int. Cl.
   *A61B 5/145*   (2006.01)
   *A61M 5/172*   (2006.01)
   *G06F 19/00*   (2018.01)
   *G06F 17/12*   (2006.01)

(52) U.S. Cl.
   CPC ......... *A61B 5/7225* (2013.01); *A61M 5/1723* (2013.01); *G06F 19/3468* (2013.01); *G16H 50/30* (2018.01); *A61M 2205/3584* (2013.01); *G06F 17/12* (2013.01); *G06F 19/3418* (2013.01)

(56) References Cited

U.S. PATENT DOCUMENTS

| | | |
|---|---|---|
| 2010/0198021 A1 | 8/2010 | Alferness et al. |
| 2012/0191361 A1 | 7/2012 | Kovatchev et al. |
| 2012/0197536 A1 | 8/2012 | Weinert et al. |
| 2014/0187887 A1 | 7/2014 | Dunn et al. |

OTHER PUBLICATIONS

Kovatchev et al.—Risk Analysis of Blood Glucose Data: A Quantitative Approach to Optimizing the Control of Insulin Dependent Diabetes; Journal of Theoretrial Medicine vol. 3. pp. 1-10 (Year: 2000).*
International Search Report (PCT/ISA/210) dated Apr. 29, 2016, by the United States Patent Office as the International Searching Authority for International Application No. PCT/US2016/018027.
Written Opinion (PCT/ISA/237) dated Apr. 29, 2016, by the United States Patent Office as the International Searching Authority for International Application No. PCT/US2016/018027.

\* cited by examiner

METHOD, SYSTEM AND COMPUTER READABLE MEDIUM FOR ASSESSING ACTIONABLE GLYCEMIC RISK

CROSS-REFERENCE TO RELATED APPLICATIONS

This application claims priority under 35 U.S.C. § 119(e) from U.S. Provisional Application Ser. No. 62/116,791, filed on Feb. 16, 2015, which is incorporated herein by reference in its entirety.

STATEMENT OF GOVERNMENT LICENSE RIGHTS

This invention was made with government support under the following contracts: NIH/NIDDK RO1 DK 08562 and 1R21EB018052-01. The U.S. Government has certain rights in the invention.

GOVERNMENT RIGHTS

This invention was made with government support under Grant Nos. DK085623 and EB018052 awarded by The National Institutes of Health. The U.S. government has certain rights in the invention.

FIELD

A system, method and non-transient computer readable medium for assessing the opportunity to address either hyperglycemic or hypoglycemic risk (or both) in patients with diabetes based on historical continuous glucose monitoring (CGM) data.

BACKGROUND

Stress-induced hyperglycemia is a common occurrence in critically ill patients [1], regardless of health status (diabetic, pre-diabetic, or metabolically normal) prior to hospital admission. Elevated blood glucose (BG) and glycemic variability have been found to contribute to infection, slow wound healing, and short-term mortality [2], [3], [4], [5], [6], [7], [8]. In groundbreaking studies from 2001-2006, G. van den Berghe and colleagues reported improved outcomes for critically ill patients, particularly cardiac surgical patients, under Tight Glycemic Control (TGC) with a plasma glucose target range of 80-110 [9], [10], [11], inspiring many hospital Intensive Care Units (ICUs) to prescribe intensive insulin therapy with aggressive glucose targets for their patients. However, subsequent attempts to replicate improved outcomes via tight glycemic control have achieved mixed results. For example, van den Berghe et al. demonstrated no improvement in mortality rates and an increase in hypoglycemic events when TGC was applied to patients in a medical ICU [12]. Results from more recent studies are even less encouraging. In particular, the 2009 multicenter study, NICE-SUGAR, found that the attempt to achieve a 81-108 mg/dl target range increases both 90 day mortality and hypoglycemic events, the latter by 13-fold [13]. Subsequently the AACE/ADA, the Endocrine Society, and the ACP have relaxed their guidelines for inpatient glycemic control, advocating a presumably safer target range of 140-180 mg/dl [14]. However, the current recommended targets are controversial [15], [16]. None of the prior studies clarify whether tight glycemic targets (e.g. BG 80-110 mg/dl) are in themselves harmful or if the danger lies in the inadequacy of the available methods for achieving and maintaining safe glycemic outcomes.

From a process control perspective, many factors may contribute to the variability of reported glycemic outcomes [14], [17], [18]. Ineffective care coordination can lead to improper implementation of an intensive insulin therapy protocol [17], [18]. Even if a protocol is implemented as intended, point-of-care device variability can affect outcomes, with errors from less than 3% to as high as 20% [14], [19], [20]. Additionally, the choice of protocol may affect the glycemic outcome for each patient. Commonly used paper-based protocols vary in target range, method of insulin delivery (intravenous and/or subcutaneous), time between measurements, practitioner adherence, nutrition support, and insulin amount prescribed for a specific blood glucose measurement or change in blood glucose over time. Thus, different protocols will have different outcomes, regardless of the institution or patient population [14], [20], [21]. For these reasons, it is not clear that simply shifting the BG target range to higher targets (e.g. 140-180 mg/dl) will result in safer outcomes for patients.

There is a clear need for modeling tools that facilitate the design of insulin therapy protocols that support the needs of specific patient populations. In vivo evaluation of alternative insulin therapy protocols (whether paper-based or computer-assisted) is expensive, time consuming, and potentially dangerous [21], [22], [23], [24], [25], and further large studies are unlikely in light of NICE-SUGAR. Moreover, it is generally infeasible to directly compare different insulin protocols in the same set of patients.

SUMMARY

An aspect of an embodiment of the present invention provides a system, method and non-transient computer readable medium for, among other things, assessing the opportunity to address either hyperglycemic or hypoglycemic risk (or both) in patients with diabetes based on historical CGM data.

An aspect of an embodiment of the present invention provides a system, method and computer readable medium for, among other things, strategically implementing aspects of diabetes treatment via retrospective analysis of continuous glucose monitoring (CGM) data.

An aspect of an embodiment of the present invention provides a system, method and computer readable medium for, among other things, implementing an initial step that may involve the assessment of blood glucose (BG) profiles (e.g., trends to high or low BG and relative risk) in retrospective analysis of CGM data. See also, for example, U.S. patent application Ser. No. 14/241,383 entitled "Method, System and Computer Readable Medium for Adaptive Advisory Control of Diabetes", filed Feb. 26, 2014; International Patent Application No. PCT/US2012/052422 entitled "Method, System and Computer Readable Medium for Adaptive Advisory Control of Diabetes", filed Aug. 26, 2012; and International Patent Application Publication No. WO 2013/032965, Mar. 7, 2013, all of which are hereby incorporated by reference in their entirety herein (and which are not admitted to be prior art with respect to the present invention by inclusion in this section).

An aspect of various embodiments of the present invention (system, method and computer readable medium) may provide a number of novel and nonobvious features, elements and characteristics, such as but not limited thereto, as follows. An aspect of an embodiment of the present invention provides a system, method and computer readable medium whereby, among other things, it (i) develops a normalized BG risk function that takes the value of one at pre-specified BG endpoints and (ii) combines the low and high BG risk profiles in a novel and nonobvious way to quantify times of the day when high and low BG risk "cancel each other out," thereby leading to an assessment of "mitigation opportunity" and "actionable risk".

An aspect of an embodiment of the present invention provides a system, method and computer readable medium that, among other things, defines an algorithmic architecture for control of diabetes that includes both live and retrospective analysis of data. See also, for example, U.S. patent application Ser. No. 13/322,943 entitled "System Coordinator and Modular Architecture for Open-Loop and Closed-Loop Control of Diabetes", filed Nov. 29, 2011; U.S. Patent Application Publication No. 2012/0078067, Mar. 29, 2012; International Patent Application No. PCT/US2010/036629 entitled "System Coordinator and Modular Architecture for Open-Loop and Closed-Loop Control of Diabetes", filed May 28, 2010; and International Patent Application Publication No. WO 2010/138848, Dec. 2, 2010, all of which are hereby incorporated by reference in their entirety herein (and which are not admitted to be prior art with respect to the present invention by inclusion in this section). An aspect of various embodiments of the present invention (system, method and computer readable medium) may provide a number of novel and nonobvious features, elements and characteristics, such as but not limited thereto, as follows: creating and applying algorithms (and techniques and methods) for retrospective analysis. Moreover, such algorithms (and techniques and methods) may be implemented by being integrated (e.g., "plug into") the modular architecture of the system or device.

An aspect of an embodiment of the present invention provides a system, method and computer readable medium for, among other things, to implement the assessment of the relative probability of hypoglycemia based on retrospective analysis of self-monitoring blood glucose (SMBG) (e.g., finger-sticks). See also, for example, U.S. patent application Ser. No. 13/394,091 entitled "Tracking the Probability for Imminent Hypoglycemia in Diabetes from Self-Monitoring Blood Glucose (SMBG) Data", filed Mar. 2, 2012; U.S. Patent Application Publication No. 2012/0191361, Jul. 26, 2012; International Patent Application No. PCT/US2010/047711 entitled "Tracking the Probability for Imminent Hypoglycemia in Diabetes from Self-Monitoring Blood Glucose (SMBG) Data", filed Sep. 2, 2010; and International Patent Application Publication No. WO 2011/028925, Mar. 10, 2011, all of which are hereby incorporated by reference in their entirety herein (and which are not admitted to be prior art with respect to the present invention by inclusion in this section). An aspect of various embodiments of the present invention (system, method and computer readable medium) may provide a number of novel and nonobvious features, elements and characteristics, such as but not limited thereto, the following: (i) it uses CGM (which may in turn be enhanced by knowledge of finger stick values, of which may be optional and not necessarily essential), (ii) it addresses both hypoglycemia and hyperglycemia, (iii) it produces a "risk assessment" (i.e., not a probability determination, for example), (iv) it provides risk assessments that are broken down into (a) "unaddressable risk" where the historical record indicates a tendency to both hypo and hyperglycemia at a given time of the day, (b) actionable hypoglycemia risk, and (c) actionable hyperglycemia risk.

BRIEF DESCRIPTION OF THE DRAWINGS

The invention can be best understood from the following detailed description of exemplary embodiments of the invention taken in conjunction with the accompanying drawings.

DETAILED DESCRIPTION OF THE DRAWINGS

Figure 1:
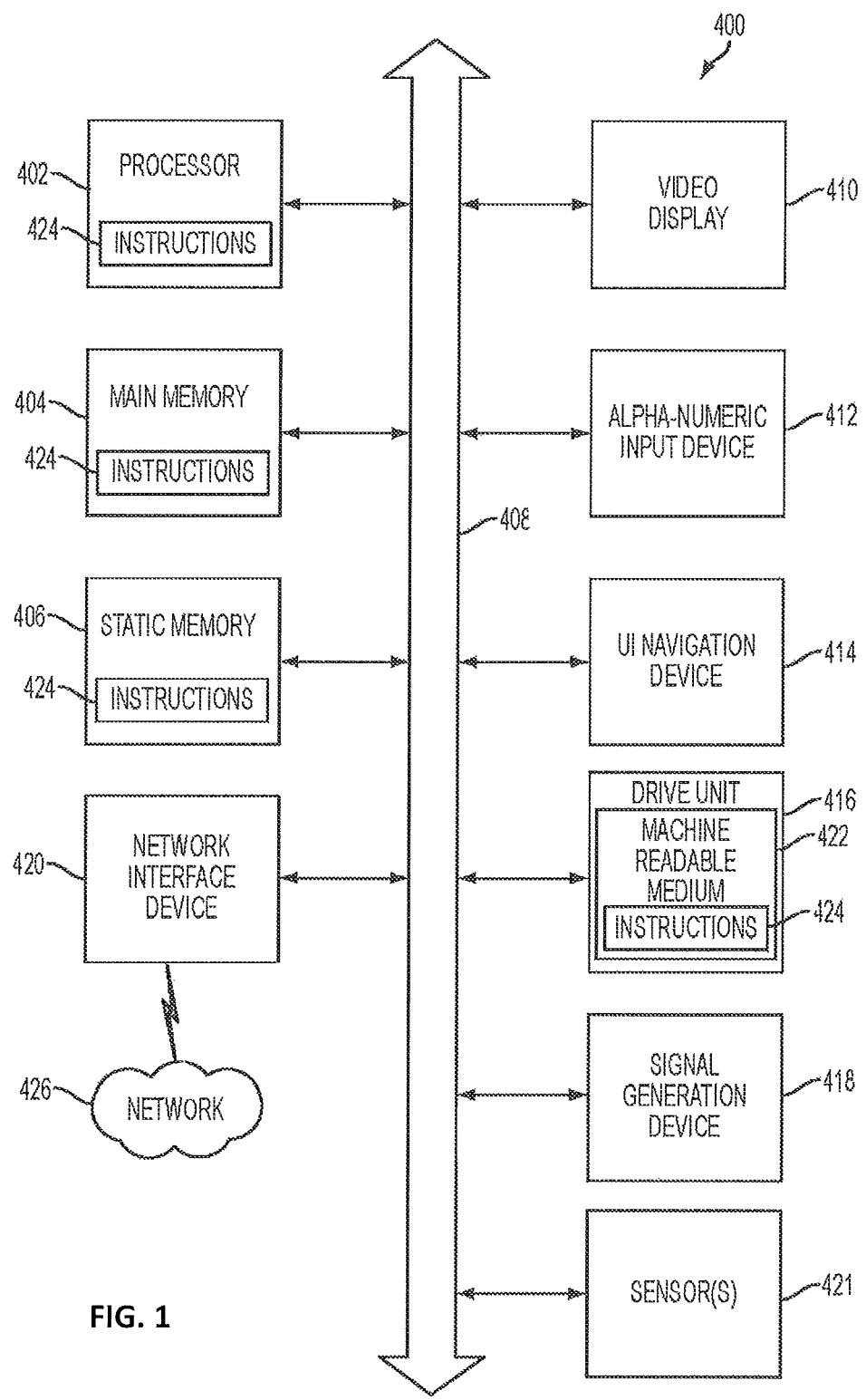
FIG. 1 is a block diagram of an example of a machine upon which one or more aspects of embodiments of the present invention can be implemented.

This invention provides a method, system, and computer readable medium for, among other things, assessing the opportunity to address either hyperglycemia or hypoglycemia risk (or both) in patients with diabetes based on historical CGM data.

In view of the many possible variations within the spirit of the invention, the invention will be discussed with reference to exemplary embodiments. However, it will be appreciated by those skilled in the art that the following discussion is for demonstration purposes, and should not be interpreted as a limitation of the invention. Other variations without departing from the spirit of the invention are applicable.

The debate about the safety and efficacy of tight glycemic control so far has been framed mainly in terms of identifying an appropriate target range of BG values. Both the proponents and detractors of tight control around euglycemic values, seem to acknowledge the inevitability of occasional hypoglycemia [20]. Interestingly, without any claims on the robustness of the insulin protocols that have been tested, it is unclear whether euglycemic targets are inherently dangerous, or whether it is simply the case that better insulin protocols need to be developed that are more sensitive to the risk of hypoglycemia. At this point, it is difficult to tell whether the clinical specification of a desired control range is a reflection of physiological requirements for plasma glucose, or whether the target range is a reelection of the inability to prevent hypoglycemic excursions. Here, we propose a simulation-based protocol optimization methodology.

Following [48], [49], [50], there is a natural asymmetry of disutility associated with BG excursions below and above euglycemia. While hyperglycemia is associated with infection and slow wound healing, the mitigation of which is the whole reason for introducing aggressive insulin therapy in the ICU, insulin overdose resulting in hypoglycemia presents a much more sever severe short term risks that be avoided. To capture this asymmetry we introduce the following asymmetric cost function designed to attribute equal cost (disutility) J to the endpoints of the desired BG target range [BGtarget,lo,BGtarget,hi]:

$$J(BG) = c\left[\ln\left(\frac{BG}{\sqrt{BG_{target,\,lo} \cdot BG_{target,\,hi}}}\right)\right]^2$$

with c chosen to ensure that J(BGtarget, lo)=J(BGtarget, hi)=1. In terms of the "shape" of J, note that J(BG)=0 when BG=BGtarget,lo·BGtarget,hi. Also, J penalizes BG excursions below BGtarget, lo much more heavily than comparable excursions above BGtarget,hi. A cost-optimal insulin protocol would be one that minimizes the expected value of $$\bar{J} = \frac{1}{N+1}\sum_{n=0}^{N} J(BG(n)).$$

across the whole population.

With continuous glucose monitoring (CGM), many type 1 patients present with high BG variability. In the face of this variability, it may be reasonable to conclude that no basal or CR changes can be justified. The notions of Actionable Risk, Actionable Hypoglycemia Risk, Actionable Hyperglycemia Risk, and Unaddressable Risk systematically quantify the degree to which (1) hypoglycemia can be addressed without increasing hyperglycemia, (2) hyperglycemia can be addressed without increasing hypoglycemia, and (3) extremes of hypo- and hyperglycemia create an unsolvable problem for the patient (without advanced treatments such as the AP).

As discussed above, a new square-of-law BG risk function has been created that can be used with different BG endpoints. The risk function always takes the same value at the endpoints of the target BG range. For example, the risk function may take the value of 1 at the endpoints of the target BG range.

In one embodiment, the BG risk function may be used to determine the Actionable Risk, Actionable Hypoglycemia Risk, Actionable Hyperglycemia Risk, and Unaddressable Risk as follows.

From the normalized risk function J, hypo- and hyperglycemia risk functions are defined, respectively:

rlo(BG)=J(BG), if BG<sqrt(BGtarget,lo*BGtarget,hi)
0,otherwise rhi(BG)=J(BG), if BG>=sqrt(BGtarget,lo*BGtarget, hi)0,otherwise The assessment of normalized low and high BG risk could optionally be enhanced with BG rate-of-change information. For example, the assessment of rlo and rhi could depend on both BG and slope(BG), where, whenever the raw assessments above are positive, the positive risk value is discounted by a factor f(slope(BG)) when BG rate-of-change indicates that the low or high BG condition is being adequately addressed.

From the instantaneous hypo- and hyperglycemia risk functions rlo and rhi, the hypo- and hyperglycemia risk profiles lop and hip are defined as moving averages over a defined interval, respectively as follows:

loma(t)=centered τ-hour moving average of rlo(BG(t)) from a CGM record hima(t)=centered τ-hour moving average of rhi(BG(t)) from a CGM record In both cases, it is necessary to "wrap around" the 24-hour day.

lop(s)=mean (across successive days) of the loma(s) value at time s of the day hip(s)=mean (across successive days) of the hima(s) value at time s of the day In one example, τ=2 hours (i.e. one hour back, one hour forward).)

A total BG risk profile may be defined from the hypo- and hyperglycemia risk profiles, lop and hip, as follows:

trp(s)=lop(s)+hip(s)

A normalized "opportunity index" may be defined associated with the mitigation opportunity. The hypoglycemia mitigation opportunity MOlow may be defined to be close to one when the total risk is explained exclusively by hypoglycemia risk.

MOlow(s)=[lop(s)−hip(s)]+/trp(s)

The actionable hypoglycemia risk may then be calculated by weighting the lop(s) by the hypoglycemia mitigation opportunity.

ARlow(s)=lop(s)*MOlow(s)

Similarly, the hyperglycemia mitigation opportunity MOhigh may be defined to be close to one when the total risk is explained exclusively by hyperglycemia risk.

MOhigh(s)=[hip(s)−lop(s)]$^+$/trp(s)

The actionable hyperglycemia risk may then be calculated by weighting the hiop(s) by the hyperglycemia mitigation opportunity.

ARhigh(s)=hip(s)*MOhigh(s)

The unaddressable risk may then be calculated based on the total risk profile, the actionable hypoglycemia risk, and the actionable hyperglycemia risk. The unaddressable risk profile may be normalized such that it is close to one when ADRR is explained exclusively by either hypo- or hyperglycemia risk, as follows.

UR(s)=[trp(s)−ARlo(s)−ARhigh(s)]/2

When processing the continuous glucose monitoring signal and generating the actionable hypoglycemia risk, actionable hyperglycemia risk, and unaddressable risk signals, it may be desired to (1) impute BGcenter values to leading null entries in the first CGM day, (2) impute BGcenter values to trailing null entries in the last CGM day, and (3) interpolate short gaps in the CGM record rather than leaving such gaps null.

In some embodiments of the invention, it may be helpful to differentiate between (and separately compute actionable risk profiles for) different kinds of treatment days. For example, data may be segregated according to different pre-programmed pump profiles (weekend v.s. weekday, work day vs. vacation), and other mitigating factors: illness, menstruation, etc.

As another optional enhancement it may be desirable to give "unaddressable risk" priority over actionable hypo or hyperglycemia risk. The mathematical equations above can simultaneously allow both positive actionable risk and unaddressable risk at a given time of the day. In presenting the results in a display, it would be possible to not highlight actionable risk when unaddressable risk at that time is significant.

Various implementations of the disclosed invention are contemplated, as explained further below. For example, actionable risk can be computed alternatively on a back-end server (in the cloud), on an aggregation device (that receives and processes CGM data locally), embedded within a CGM receiver, or embedded within combination CGM/pump device. Various implementations may also include a digital processor, a continuous blood glucose sensor, and a risk determination module. In yet other embodiments, a non-transient computer readable medium may have instructions stored thereon configured to cause the digital processor to implement one or more of the methods disclosed herein.

In some embodiments, one or more of the total risk profile, actionable hypoglycemia risk, actionable hyperglycemia risk, and unaddressable risk may be graphically illustrated to assist in communicating the assessment of glycemic risk to the patient or medical professionals.

FIG. 1 is a block diagram illustrating an example of a machine upon which one or more aspects of embodiments of the present invention can be implemented.

FIG. 1 illustrates a block diagram of an example machine 400 upon which one or more embodiments (e.g., discussed methodologies) can be implemented (e.g., run).

Examples of machine 400 can include logic, one or more components, circuits (e.g., modules), or mechanisms. Circuits are tangible entities configured to perform certain operations. In an example, circuits can be arranged (e.g., internally or with respect to external entities such as other circuits) in a specified manner. In an example, one or more computer systems (e.g., a standalone, client or server computer system) or one or more hardware processors (processors) can be configured by software (e.g., instructions, an application portion, or an application) as a circuit that operates to perform certain operations as described herein. In an example, the software can reside (1) on a non-transitory machine readable medium or (2) in a transmission signal. In an example, the software, when executed by the underlying hardware of the circuit, causes the circuit to perform the certain operations.

In an example, a circuit can be implemented mechanically or electronically. For example, a circuit can comprise dedicated circuitry or logic that is specifically configured to perform one or more techniques such as discussed above, such as including a special-purpose processor, a field programmable gate array (FPGA) or an application-specific integrated circuit (ASIC). In an example, a circuit can comprise programmable logic (e.g., circuitry, as encompassed within a general-purpose processor or other programmable processor) that can be temporarily configured (e.g., by software) to perform the certain operations. It will be appreciated that the decision to implement a circuit mechanically (e.g., in dedicated and permanently configured circuitry), or in temporarily configured circuitry (e.g., configured by software) can be driven by cost and time considerations.

Accordingly, the term "circuit" is understood to encompass a tangible entity, be that an entity that is physically constructed, permanently configured (e.g., hardwired), or temporarily (e.g., transitorily) configured (e.g., programmed) to operate in a specified manner or to perform specified operations. In an example, given a plurality of temporarily configured circuits, each of the circuits need not be configured or instantiated at any one instance in time. For example, where the circuits comprise a general-purpose processor configured via software, the general-purpose processor can be configured as respective different circuits at different times. Software can accordingly configure a processor, for example, to constitute a particular circuit at one instance of time and to constitute a different circuit at a different instance of time.

In an example, circuits can provide information to, and receive information from, other circuits. In this example, the circuits can be regarded as being communicatively coupled to one or more other circuits. Where multiple of such circuits exist contemporaneously, communications can be achieved through signal transmission (e.g., over appropriate circuits and buses) that connect the circuits. In embodiments in which multiple circuits are configured or instantiated at different times, communications between such circuits can be achieved, for example, through the storage and retrieval of information in memory structures to which the multiple circuits have access. For example, one circuit can perform an operation and store the output of that operation in a memory device to which it is communicatively coupled. A further circuit can then, at a later time, access the memory device to retrieve and process the stored output. In an example, circuits can be configured to initiate or receive communications with input or output devices and can operate on a resource (e.g., a collection of information).

The various operations of method examples described herein can be performed, at least partially, by one or more processors that are temporarily configured (e.g., by software) or permanently configured to perform the relevant operations. Whether temporarily or permanently configured, such processors can constitute processor-implemented circuits that operate to perform one or more operations or functions. In an example, the circuits referred to herein can comprise processor-implemented circuits.

Similarly, the methods described herein can be at least partially processor-implemented. For example, at least some of the operations of a method can be performed by one or processors or processor-implemented circuits. The performance of certain of the operations can be distributed among the one or more processors, not only residing within a single machine, but deployed across a number of machines. In an example, the processor or processors can be located in a single location (e.g., within a home environment, an office environment or as a server farm), while in other examples the processors can be distributed across a number of locations.

The one or more processors can also operate to support performance of the relevant operations in a "cloud computing" environment or as a "software as a service" (SaaS). For example, at least some of the operations can be performed by a group of computers (as examples of machines including processors), with these operations being accessible via a network (e.g., the Internet) and via one or more appropriate interfaces (e.g., Application Program Interfaces (APIs).)

Example embodiments (e.g., apparatus, systems, or methods) can be implemented in digital electronic circuitry, in computer hardware, in firmware, in software, or in any combination thereof. Example embodiments can be implemented using a computer program product (e.g., a computer program, tangibly embodied in an information carrier or in a machine readable medium, for execution by, or to control the operation of, data processing apparatus such as a programmable processor, a computer, or multiple computers).

A computer program can be written in any form of programming language, including compiled or interpreted languages, and it can be deployed in any form, including as a stand-alone program or as a software module, subroutine, or other unit suitable for use in a computing environment. A computer program can be deployed to be executed on one computer or on multiple computers at one site or distributed across multiple sites and interconnected by a communication network.

In an example, operations can be performed by one or more programmable processors executing a computer program to perform functions by operating on input data and generating output. Examples of method operations can also be performed by, and example apparatus can be implemented as, special purpose logic circuitry (e.g., a field programmable gate array (FPGA) or an application-specific integrated circuit (ASIC)).

The computing system can include clients and servers. A client and server are generally remote from each other and generally interact through a communication network. The relationship of client and server arises by virtue of computer programs running on the respective computers and having a client-server relationship to each other. In embodiments deploying a programmable computing system, it will be appreciated that both hardware and software architectures require consideration. Specifically, it will be appreciated that the choice of whether to implement certain functionality in permanently configured hardware (e.g., an ASIC), in temporarily configured hardware (e.g., a combination of software and a programmable processor), or a combination of permanently and temporarily configured hardware can be a design choice. Below are set out hardware (e.g., machine 400) and software architectures that can be deployed in example embodiments.

In an example, the machine 400 can operate as a standalone device or the machine 400 can be connected (e.g., networked) to other machines.

In a networked deployment, the machine 400 can operate in the capacity of either a server or a client machine in server-client network environments. In an example, machine 400 can act as a peer machine in peer-to-peer (or other distributed) network environments. The machine 400 can be a personal computer (PC), a tablet PC, a set-top box (STB), a Personal Digital Assistant (PDA), a mobile telephone, a web appliance, a network router, switch or bridge, or any machine capable of executing instructions (sequential or otherwise) specifying actions to be taken (e.g., performed) by the machine 400. Further, while only a single machine 400 is illustrated, the term "machine" shall also be taken to include any collection of machines that individually or jointly execute a set (or multiple sets) of instructions to perform any one or more of the methodologies discussed herein.

Example machine (e.g., computer system) 400 can include a processor 402 (e.g., a central processing unit (CPU), a graphics processing unit (GPU) or both), a main memory 404 and a static memory 406, some or all of which can communicate with each other via a bus 408. The machine 400 can further include a display unit 410, an alphanumeric input device 412 (e.g., a keyboard), and a user interface (UI) navigation device 411 (e.g., a mouse). In an example, the display unit 810, input device 417 and UI navigation device 414 can be a touch screen display. The machine 400 can additionally include a storage device (e.g., drive unit) 416, a signal generation device 418 (e.g., a speaker), a network interface device 420, and one or more sensors 421, such as a global positioning system (GPS) sensor, compass, accelerometer, or other sensor.

The storage device 416 can include a machine readable medium 422 on which is stored one or more sets of data structures or instructions 424 (e.g., software) embodying or utilized by any one or more of the methodologies or functions described herein. The instructions 424 can also reside, completely or at least partially, within the main memory 404, within static memory 406, or within the processor 402 during execution thereof by the machine 400. In an example, one or any combination of the processor 402, the main memory 404, the static memory 406, or the storage device 416 can constitute machine readable media.

While the machine readable medium 422 is illustrated as a single medium, the term "machine readable medium" can include a single medium or multiple media (e.g., a centralized or distributed database, and/or associated caches and servers) that configured to store the one or more instructions 424. The term "machine readable medium" can also be taken to include any tangible medium that is capable of storing, encoding, or carrying instructions for execution by the machine and that cause the machine to perform any one or more of the methodologies of the present disclosure or that is capable of storing, encoding or carrying data structures utilized by or associated with such instructions. The term "machine readable medium" can accordingly be taken to include, but not be limited to, solid-state memories, and optical and magnetic media. Specific examples of machine readable media can include non-volatile memory, including, by way of example, semiconductor memory devices (e.g., Electrically Programmable Read-Only Memory (EPROM), Electrically Erasable Programmable Read-Only Memory (EEPROM)) and flash memory devices; magnetic disks such as internal hard disks and removable disks; magneto-optical disks; and CD-ROM and DVD-ROM disks.

The instructions 424 can further be transmitted or received over a communications network 426 using a transmission medium via the network interface device 420 utilizing any one of a number of transfer protocols (e.g., frame relay, IP, TCP, UDP, HTTP, etc.). Example communication networks can include a local area network (LAN), a wide area network (WAN), a packet data network (e.g., the Internet), mobile telephone networks (e.g., cellular networks), Plain Old Telephone (POTS) networks, and wireless data networks (e.g., IEEE 802.11 standards family known as Wi-Fi®, IEEE 802.16 standards family known as WiMax®), peer-to-peer (P2P) networks, among others. The term "transmission medium" shall be taken to include any intangible medium that is capable of storing, encoding or carrying instructions for execution by the machine, and includes digital or analog communications signals or other intangible medium to facilitate communication of such software.

Figure 2:
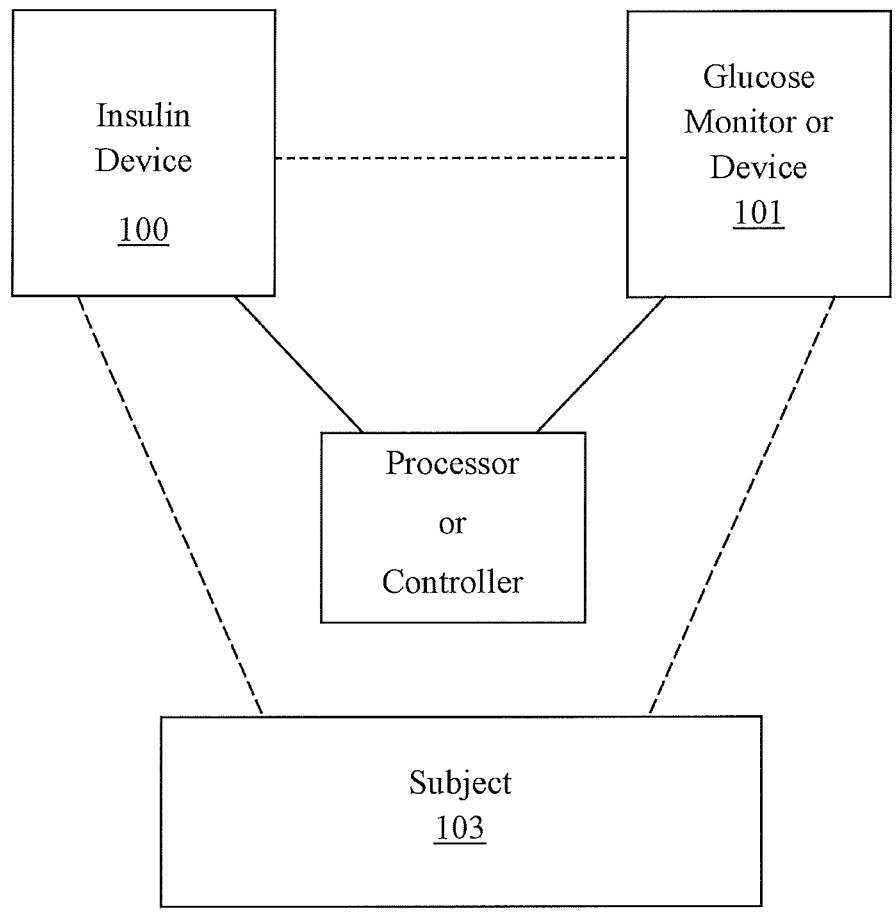
FIG. 2 is a high level functional block diagram of an embodiment of the invention.

FIG. 2 is a high level functional block diagram of an embodiment of the invention.

As shown in FIG. 2, a processor or controller 102 may communicate with the glucose monitor or device 101, and optionally the insulin device 100. The glucose monitor or device 101 may communicate with the subject 103 to monitor glucose levels of the subject 103. The processor or controller 102 is configured to perform the required calculations. Optionally, the insulin device 100 may communicate with the subject 103 to deliver insulin to the subject 103. The processor or controller 102 is configured to perform the required calculations. The glucose monitor 101 and the insulin device 100 may be implemented as a separate device or as a single device. The processor 102 can be implemented locally in the glucose monitor 101, the insulin device 100, or a standalone device (or in any combination of two or more of the glucose monitor, insulin device, or a stand along device). The processor 102 or a portion of the system can be located remotely such that the device is operated as a telemedicine device.

Referring to FIG. 3, in its most basic configuration, computing device 144 typically includes at least one processing unit 150 and memory 146. Depending on the exact configuration and type of computing device, memory 146 can be volatile (such as RAM), non-volatile (such as ROM, flash memory, etc.) or some combination of the two.

Additionally, device 144 may also have other features and/or functionality. For example, the device could also include additional removable and/or non-removable storage including, but not limited to, magnetic or optical disks or tape, as well as writable electrical storage media. Such additional storage is the figure by removable storage 152 and non-removable storage 148. Computer storage media includes volatile and nonvolatile, removable and non-removable media implemented in any method or technology for storage of information such as computer readable instructions, data structures, program modules or other data. The memory, the removable storage and the non-removable storage are all examples of computer storage media. Computer storage media includes, but is not limited to, RAM, ROM, EEPROM, flash memory or other memory technology CDROM, digital versatile disks (DVD) or other optical storage, magnetic cassettes, magnetic tape, magnetic disk storage or other magnetic storage devices, or any other medium which can be used to store the desired information and which can accessed by the device. Any such computer storage media may be part of, or used in conjunction with, the device.

The device may also contain one or more communications connections 154 that allow the device to communicate with other devices (e.g. other computing devices). The communications connections carry information in a communication media. Communication media typically embodies computer readable instructions, data structures, program modules or other data in a modulated data signal such as a carrier wave or other transport mechanism and includes any information delivery media. The term "modulated data signal" means a signal that has one or more of its characteristics set or changed in such a manner as to encode, execute, or process information in the signal. By way of example, and not limitation, communication medium includes wired media such as a wired network or direct-wired connection, and wireless media such as radio, RF, infrared and other wireless media. As discussed above, the term computer readable media as used herein includes both storage media and communication media.

Figure 3A:
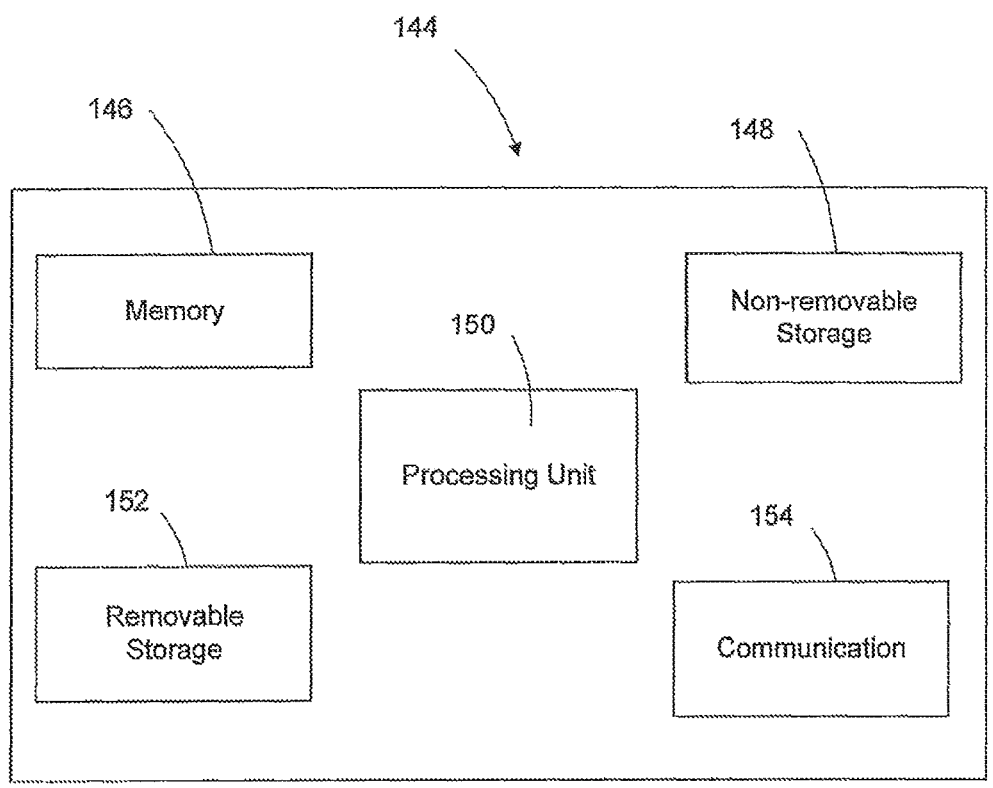
FIG. 3A is a block diagram of a computing device upon which one or more aspects of embodiments of the invention can be implemented.
Figure 3B:
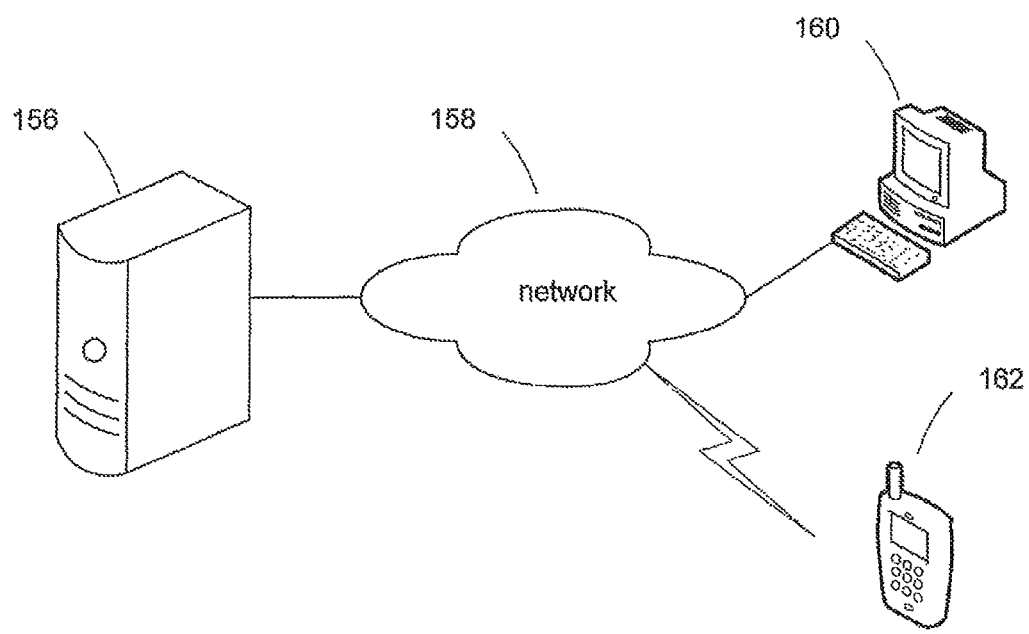
FIG. 3B illustrates a network system upon which one or more aspects of embodiments of the invention can be implemented.

In addition to a stand-alone computing machine, embodiments of the invention can also be implemented on a network system comprising a plurality of computing devices that are in communication with a networking means, such as a network with an infrastructure or an ad hoc network. The network connection can be wired connections or wireless connections. As a way of example, FIG. 3B illustrates a network system in which embodiments of the invention can be implemented. In this example, the network system comprises computer 156 (e.g. a network server), network connection means 158 (e.g. wired and/or wireless connections), computer terminal 160, and PDA (e.g. a smart-phone) 162 (or other handheld or portable device, such as a cell phone, laptop computer, tablet computer, GPS receiver, mp3 player, handheld video player, pocket projector, etc. or handheld devices (or non portable devices) with combinations of such features). In an embodiment, it should be appreciated that the module listed as 156 may be glucose monitor device. In an embodiment, it should be appreciated that the module listed as 156 may be a glucose monitor device and an insulin device. Any of the components shown or discussed with FIG. 3A may be multiple in number. The embodiments of the invention can be implemented in anyone of the devices of the system. For example, execution of the instructions or other desired processing can be performed on the same computing device that is anyone of 156, 160, and 162. Alternatively, an embodiment of the invention can be performed on different computing devices of the network system. For example, certain desired or required processing or execution can be performed on one of the computing devices of the network (e.g. server 156 and/or glucose monitor device), whereas other processing and execution of the instruction can be performed at another computing device (e.g. terminal 160) of the network system, or vice versa. In fact, certain processing or execution can be performed at one computing device (e.g. server 156 and/or glucose monitor device); and the other processing or execution of the instructions can be performed at different computing devices that may or may not be networked. For example, the certain processing can be performed at terminal 160, while the other processing or instructions are passed to device 162 where the instructions are executed. This scenario may be of particular value especially when the PDA 162 device, for example, accesses to the network through computer terminal 160 (or an access point in an ad hoc network). For another example, software to be protected can be executed, encoded or processed with one or more embodiments of the invention. The processed, encoded or executed software can then be distributed to customers. The distribution can be in a form of storage media (e.g. disk) or electronic copy.

Figure 4:
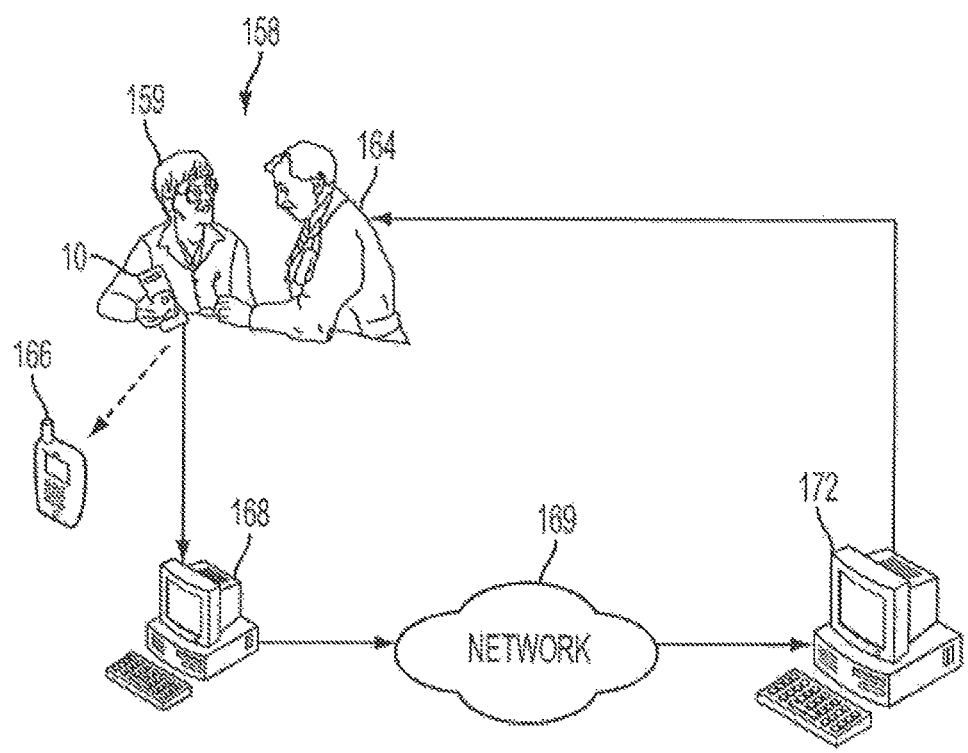
FIG. 4 illustrates a system in which one or more embodiments of the invention can be implemented using a network, or portions of a network or computers.

FIG. 4 illustrates a system in which one or more embodiments of the invention can be implemented using a network, or portions of a network or computers.

FIG. 4 diagrammatically illustrates an exemplary system in which examples of the invention can be implemented. In an embodiment the glucose monitor may be implemented by the subject (or patient) at home or other desired location. However, in an alternative embodiment it may be implemented in a clinic setting or assistance setting. For instance, referring to FIG. 4, a clinic setup 158 provides a place for doctors (e.g. 164) or clinician/assistant to diagnose patients (e.g. 159) with diseases related with glucose. A glucose monitoring device 10 (and/or insulin pump device or pump) can be used to monitor and/or test the glucose levels of the patient. It should be appreciated that while only glucose monitor device 10 is shown in the figure, the system of the invention and any component thereof may be used in the manner depicted by FIG. 4. The system or component may be affixed to the patient or in communication with the patient as desired or required. For example the system or combination of components thereof—including a glucose monitor device 10, a controller 12, or an insulin pump 14, or any other device or component—may be in contact or affixed to the patient through tape or tubing or may be in communication through wired or wireless connections. Such monitor and/or test can be short term (e.g. clinical visit) or long term (e.g. clinical stay or family). The glucose monitoring device outputs can be used by the doctor (clinician or assistant) for appropriate actions, such as insulin injection or food feeding for the patient, or other appropriate actions. Alternatively, the glucose monitoring device output can be delivered to computer terminal 168 for instant or future analyses. The delivery can be through cable or wireless or any other suitable medium. The glucose monitoring device output from the patient can also be delivered to a portable device, such as PDA 166. The glucose monitoring device outputs with improved accuracy can be delivered to a glucose monitoring center 172 for processing and/or analyzing. Such delivery can be accomplished in many ways, such as network connection 170, which can be wired or wireless.

In addition to the glucose monitoring device outputs, errors, parameters for accuracy improvements, and any accuracy related information can be delivered, such as to computer 168, and/or glucose monitoring center 172 for performing error analyses. This can provide a centralized accuracy monitoring and/or accuracy enhancement for glucose centers, due to the importance of the glucose sensors.

Examples of the invention can also be implemented in a standalone computing device associated with the target glucose monitoring device. An exemplary computing device in which examples of the invention can be implemented is schematically illustrated in FIG. 3A.

The following patents, applications and publications as listed below and throughout this document are hereby incorporated by reference in their entirety herein (and which are not admitted to be prior art with respect to the present invention by inclusion in this section).

[1] K. C. McCowen, A. Malhotra, and B. R. Bistrian, "Stress-induced hyperglycemia," Critical Care Clinics, vol. 17, no. 1, pp. 107-124, 2001.

[2] D. C. Gore, D. Chinkes, J. Heggers, D. N. Herndon, S. E. Wolf, and M. Desai, "Association of hyperglycemia with increased mortality after severe burn injury," Journal of Trauma and Acute Care Surgery, vol. 51, no. 3, pp. 540-544, 2001.

[3] J. S. Krinsley, "Association between hyperglycemia and increased hospital mortality in a heterogeneous population of critically ill patients," Mayo Clinic Proceedings, vol. 78, pp. 1471-1478, 2003.

[4] S. O. Butler, I. F. Btaiche, and C. Alaniz, "Relationship between hyperglycemia and infection in critically ill patients," Pharmacotherapy: The Journal of Human Pharmacology and Drug Therapy, vol. 25, no. 7, pp. 963-976, 2005.

[5] N. W. Cheung, B. Napier, C. Zaccaria, and J. P. Fletcher, "Hyperglycemia is associated with adverse outcomes in patients receiving total parenteral nutrition," Dia Care, vol. 28, no. 10, pp. 2367-237', 2005.

[6] S. C. Gale, C. Sicoutris, P. M. Reilly, C. W. Schwab, and V. H. Gracias, "Poor glycemic control is associated with increased mortality in critically ill trauma patients," American Surgeon, vol. 73, no. 5, pp. 454-460, 2007.

[7] M. Egi, R. Bellomo, E. Stachowski, C. J. French, G. K. Hart, G. Taori, C. Hegarty, and M. Bailey, "Hypoglycemia and outcome in critically ill patients," Mayo Clinic Proceedings, vol. 85, no. 3, pp. 217-224, 2010.

[8] G. V. Bochicchio, J. Sung, M. Joshi, K. Bochicchio, S. B. Johnson, W. Meyer, and T. M. Scalea, "Persistent hyperglycemia is predictive of outcome in critically ill trauma patients," J Trauma, vol. 58, no. 5, pp. 921-924, 2005.

[9] G. Van den Berghe, P. Wouters, F. Weekers, C. Verwaest, F. Bruyn-inckx, M. Schetz, D. Vlasselaers, P. Ferdinande, P. Lauwers, and R. Bouillon, "Intensive insulin therapy in critically ill patients," New England Journal of Medicine, vol. 345, no. 19, pp. 1359-1367, 2001.

[10] G. Van den Berghe, A. Wilmer, I. Milants, P. J. Wouters, B. Bouckaert, F. Bruyninckx, R. Bouillon, and M. Schetz, "Intensive insulin therapy in mixed medical/surgical intensive care units benefit versus harm," Diabetes, vol. 55, no. 11, pp. 3151-3159, 2006.

[11] A. G. Pittas, R. D. Siegel, and J. Lau, "Insulin therapy for critically ill hospitalized patients: A meta-analysis of randomized controlled trials," Arch Intern Med, vol. 164, no. 18, pp. 2005-2011, 2004.

[12] G. Van den Berghe, A. Wilmer, G. Hermans, W. Meersseman, P. J. Wouters, I. Milants, E. Van Wijngaerden, H. Bobbaers, and R. Bouillon, "Intensive insulin therapy in the medical icu," New England Journal of Medicine, vol. 354, no. 5, pp. 449-461, 2006.

[13] T. N.-S. S. Investigators, "Intensive versus conventional glucose control in critically ill patients," New England Journal of Medicine, vol. 360, no. 13, pp. 1283-1297, 2009.

[14] E. S. Moghissi, M. T. Korytkowski, M. DiNardo, D. Einhorn, R. Hellman, I. B. Hirsch, S. E. Inzucchi, F. Ismail-Beigi, M. S. Kirkman, and G. E. Umpierrez, "American association of clinical endocrinologists and american diabetes association consensus statement on inpatient glycemic control," Diabetes Care, vol. 32, no. 6, pp. 1119-1131, 2009.

[15] D. Kansagara, R. Fu, M. Freeman, F. Wolf, and M. Helfand, "Intensive insulin therapy in hospitalized patients: a systematic review," Ann. Intern. Med., vol. 154, no. 4, pp. 268-282, 2011.

[16] M. J. Lanspa, E. L. Hirshberg, G. D. Phillips, J. Holmen, G. Stoddard, and J. Orme, "Moderate glucose control is associated with increased mortality compared to tight glucose control in critically ill non-diabetics," 2013, vol. 143, no. 5, pp. 1226-1234, Chest.

[17] K. E. Anger and P. M. Szumita, "Barriers to glucose control in the intensive care unit," Pharmacotherapy: The Journal of Human Pharmacology and Drug Therapy, vol. 26, no. 2, pp. 214-228, 2006.

[18] D. Aragon, "Evaluation of nursing work effort and perceptions about blood glucose testing in tight glycemic control," Am J Crit Care, vol. 15, no. 4, pp. 370-377, 2006.

[19] J. G. Chase, G. M. Shaw, X. W. Wong, Lotz, J. Lin, and C. E. Hann, "Model-based glycaemic control in critical care-a review of the state of the possible," Biomedical Signal Processing and Control, vol. 1, no. 1, pp. 3-21, 2006.

[20] D. Mesotten and G. Van den Berghe, "Glycemic targets and approaches to management of the patient with critical illness," Curren Diab Rep, vol. 12, no. 1, pp. 101-107, 2012.

[21] J. Blaha, P. Kopecky, M. Matias, R. Hovorka, J. Kunstyr, T. Kotu-lak, M. Lips, D. Rubes, M. Stritesky, J. Lindner, M. Semrad, and M. Haluzik, "Comparison of three protocols for tight glycemic control in cardiac surgery patients," Dia Care, vol. 32, no. 5, pp. 757-761, 2009.

[22] J. G. Chase, G. Shaw, A. Le Compte, T. Lonergan, M. Willacy, X.-W. Wong, J. Lin, T. Lotz, D. L. D, and C. Hann, "Implementation and evaluation of the sprint protocol for tight glycaemic control in critically ill patients: a clinical practice change," Critical Care, vol. 12, no. 2, p. R49, 2008.

[23] J. G. Chase, G. M. Shaw, T. Lotz, A. Le Compte, J. Wong, J. Lin, T. Lonergan, M. Willacy, and C. E. Hann, "Model-based insulin and nutrition administration for tight glycaemic control in critical care," Current Drug Delivery, vol. 4, no. 4, pp. 283-296, 2007.

[24] J.-C. Preiser, P. Devos, S. Ruiz-Santana, C. Mélot, D. Annane, J. Groeneveld, G. Iapichino, X. Leverve, G. Nitenberg, P. Singer, J. Wernerman, M. Joannidis, A. Stecher, and R. Chioléro, "A prospective randomised multi-centre controlled trial on tight glucose control by intensive insulin therapy in adult intensive care units: the glucontrol study," Intensive Care Medicine, vol. 35, no. 10, pp. 1738-1748, 2009.

[25] G. D. C. De La Rosa, J. H. Donado, A. H. Restrepo, A. M. Quintero, L. G. Gonz'alez, N. E. Saldarriaga, M. Bedoya, J. M. Toro, J. B. Vel'asquez, and J. C. Valencia, "Strict glycaemic control in patients hospitalised in a mixed medical and surgical intensive care unit: a randomised clinical trial," Critical Care, vol. 12, no. 5, p. R120, 2008.

[26] A. Rostami-Hodjegan and G. Tucker, "In silico simulations to assess the in vivo consequences of in vitro

[27] A. Rostami-Hodjegan and G. T. Tucker, "Simulation and prediction of in vivo drug metabolism in human populations from in vitro data," Nature Reviews Drug Discovery, vol. 6, no. 2, pp. 140-148, 2007.

[28] S. Michelson, A. Sehgal, and C. Friedrich, "In silico prediction of clinical efficacy," Current opinion in biotechnology, vol. 17, no. 6, pp. 666-670, 2006.

[29] B. Kovatchev, M. Breton, C. Dalla Man, and C. Cobelli, "In Silico preclinical trials: A proof of concept in closed-loop control of type 1 diabetes," J Diab Sci and Tech, vol. 3, pp. 44-55, 2009.

[30] S. D. Patek, B. W. Bequette, M. Breton, B. A. Buckingham, E. Dassau, F. J. Doyle I I I, J. Lum, L. Magni, and H. Zisser, "In Silico Preclinical Trials: Methodology and Engineering Guide to Closed-Loop Control in Type 1 Diabetes Mellitus," J Diab Sci and Tech, vol. 3, pp. 269-282, 2009.

[31] C. Dalla Man, F. Micheletto, D. Lv, M. Breton, B. Kovatchev, and C. Cobelli, "The uva/padova type 1 diabetes simulator: New features," J Diabetes Sci Technol, vol. 8, no. 1, pp. 26-34, 2014.

[32] C. Dalla Man, R. A. Rizza, and C. Cobelli, "Meal simulation model of the glucose-insulin system," IEEE Trans Biomedical Eng, vol. 54, no. 10, pp. 1740-1749, 2007.

[33] J. G. Chase, G. M. Shaw, J. Lin, C. V. Doran, C. Hann, M. B. Robertson, P. M. Browne, T. Lotz, G. C. Wake, and B. Broughton, "Adaptive bolus-based targeted glucose regulation of hyperglycaemia in critical care," Med Eng Phys, vol. 27, no. 1, pp. 1-11, 2005.

[34] R. Hovorka, L. J. Chassin, M. Ellmerer, J. Plank, and M. E. Wilinska, "A simulation model of glucose regulation in the critically ill," Physiol Meas, vol. 29, no. 8, pp. 959-978, 2008.

[35] T. V. Herpe, M. Espinoza, N. Haverbeke, B. D. Moor, and G. Van den Berghe, "Glycemia prediction in critically ill patients using an adaptive modeling approach," J Diabetes Sci Technol, vol. 1, no. 3, pp. 348-356, 2007.

[36] J. G. Chase, F. Suhaimi, S. Penning, J.-C. Preiser, A. J. Le Compte, J. Lin, C. G. Pretty, G. M. Shaw, K. T. Moorhead, and T. Desaive, "Validation of a model-based virtual trials method for tight glycemic control in intensive care," Biomed Eng Online, vol. 9, p. 84, 2010.

[37] M. E. Wilinska, J. Blaha, L. J. Chassin, J. J. Cordingley, N. C. Dormand, M. Ellmerer, M. Haluzik, J. Plank, D. Vlasselaers, P. J. Wouters, and R. Hovorka, "Evaluating glycemic control algorithms by computer simulations," Diabetes Technol. Ther., vol. 13, no. 7, pp. 713-722, 2011.

[38] E. A. Ortiz et al., "Ortiz ms manuscript [fix]," 2014.

[39] J. G. Chase, A. Le Compte, G. M. Shaw, A. Blakemore, J. Wong, J. Lin, and C. E. Hann, "A benchmark data set for model-based glycemic control in critical care," J Diabetes Sci Technol, vol. 2, no. 4, pp. 584-594, 2008.

[40] G. M. Steil, D. Deiss, J. Shih, B. Buckingham, S. Weinzimer, and

[41] M. S. Agus, "Intensive care unit insulin delivery algorithms: Why so many?how to choose?" J Diabetes Sci Technol, vol. 3, no. 1, pp. 125-140, 2009.

[42] P. A. G. PA, M. D. Siegel, R. S. Sherwin, J. I. Halickman, M. Lee, V. A. Bailey, S. L. Lee, J. D. Dziura, and S. E. Inzucchi, "Implementation of a safe and effective insulin infusion protocol in a medical intensive care unit," Diabetes Care, vol. 27, no. 2, pp. 461-467, 2004.

[43] D. L. Trence, J. L. Kelly, and I. B. Hirsch, "The rationale and management of hyperglycemia for in-patients with cardiovascular disease: time for change," J Clin Endocrinol Metab, vol. 88, no. 6, pp. 2430-2437, 2003.

[44] E. Rood, R. J. Bosman, J. I. Van Der Spoel, P. TAYLOR, and D. F. Zandstra, "Use of a computerized guideline for glucose regulation in the intensive care unit improved both guideline adherence and glucose regulation," J Am Med Inform Assoc, vol. 12, no. 2, pp. 172-180, 2005.

[45] C. G. L. Cao, A. Ozdas, and J. Slagle, "Utilization of computerized order entry protocols in the icu for glucose management," in Proceedings IEA2006 World Congress on Ergonomics, 2006.

[46] J. B. Boord, M. Sharifi, R. A. Greevy, M. R. Griffent, V. K. Lee, T. A. Webb, M. E. May, L. R. Waitman, A. K. May, and R. A. Miller, "Computer-based insulin infusion protocol improves glycemia control over manual protocol," J Am Med Inform Assoc, vol. 14, no. 3, pp. 278-287, 2007.

[47] P. Davidson, R. Steed, and B. Bode, "Glucommander a computer-directed intravenous insulin system shown to be safe, simple, and effective in 120, 618 h of operation," Diabetes Care, vol. 28, no. 10, pp. 2418-2423, 2005.

[48] R. Juneja, C. P. Roudebush, S. A. Nasraway, A. A. Golas, J. Jacobi, J. Carroll, D. Nelson, V. J. Abad, and S. J. Flanders, "Computerized intensive insulin dosing can mitigate hypoglycemia and achieve tight glycemic control when glucose measurement is performed frequently and on time," Critical Care, vol. 13, no. 5, p. R163, 2009.

[49] B. Kovatchev, M. Straume, D. Cox, and L. Farhy, "Risk analysis of blood glucose data: a quantitative approach to optimizing the control of insulin dependent diabetes," J Theor Med, vol. 3, pp. 1-10, 2001.

[50] L. S. Farhy, E. A. Ortiz, B. P. Kovatchev, A. G. Mora, S. E. Wolf, and C. E. Wade, "Average daily risk range as a measure of glycemic risk is associated with mortality in the intensive care unit: A retrospective study in a burn intensive care unit," J Diabetes Sci Technol, vol. 5, no. 5, pp. 1087-1098, 2011.

[51] S. D. Patek, M. Breton, P. Vereshchetin, B. Jiang, and B. P. Kovatchev, "Model-Based Control of Type 1 Diabetes in "Risk Space"," in IFAC World Congress, 2014.

The devices, systems, non-transitory computer readable medium, and methods of various embodiments of the invention disclosed herein may utilize aspects disclosed in the following references, applications, publications and patents and which are hereby incorporated by reference herein in their entirety (and which are not admitted to be prior art with respect to the present invention by inclusion in this section):

a. U.S. patent application Ser. No. 14/419,375 entitled "Computer Simulation for Testing and Monitoring of Treatment Strategies for Stress Hyperglycemia", filed Feb. 3, 2015.

b. International Patent Application No. PCT/US2013/053664 entitled "Computer Simulation for Testing and Monitoring of Treatment Strategies for Stress Hyperglycemia", filed Aug. 5, 2013; International Patent Application Publication No. WO 2014/022864, Feb. 6, 2014.

c. International Patent Application No. PCT/US2015/010167 entitled "Central Data Exchange Node For System Monitoring and Control of Blood Glucose Levels in Diabetic Patients", filed Jan. 5, 2015.

d. International Patent Application No. PCT/US2014/045393 entitled "Simulation of Endogenous and Exogenous Glucose/Insulin/Glucagon Interplay in Type 1 Diabetic Patients", filed Jul. 3, 2014.

e. U.S. patent application Ser. No. 14/266,612 entitled "Method, System and Computer Program Product for Real-Time Detection of Sensitivity Decline in Analyte Sensors", filed Apr. 30, 2014; U.S. Patent Application Publication No. 2014/0244216, Aug. 28, 2014.
f. U.S. patent application Ser. No. 13/418,305 entitled "Method, System and Computer Program Product for Real-Time Detection of Sensitivity Decline in Analyte Sensors", filed Mar. 12, 2012; U.S. Pat. No. 8,718,958, issued May 6, 2014.
g. International Patent Application No. PCT/US2007/082744 entitled "Method, System and Computer Program Product for Real-Time Detection of Sensitivity Decline in Analyte Sensors", filed Oct. 26, 2007; International Patent Application Publication No. WO/2008/052199, May 2, 2008.
h. U.S. patent application Ser. No. 11/925,689 entitled "Method, System and Computer Program Product for Real-Time Detection of Sensitivity Decline in Analyte Sensors", filed Oct. 26, 2007; U.S. Pat. No. 8,135,548, issued Mar. 13, 2012.
i. U.S. patent application Ser. No. 14/241,383 entitled "Method, System and Computer Readable Medium for Adaptive Advisory Control of Diabetes", filed Feb. 26, 2014.
j. International Patent Application No. PCT/US2012/052422 entitled "Method, System and Computer Readable Medium for Adaptive Advisory Control of Diabetes", filed Aug. 26, 2012; International Patent Application Publication No. WO 2013/032965, Mar. 7, 2013.
k. International Patent Application No. PCT/US2014/017754 entitled "Method and System for Model-Based Tracking of Changes in Average Glycemia in Diabetes", filed Feb. 21, 2014; International Patent Application Publication No. WO 2014/130841, Aug. 28, 2014.
l. U.S. patent application Ser. No. 14/128,922 entitled "Unified Platform For Monitoring and Control of Blood Glucose Levels in Diabetic Patients", filed Dec. 23, 2013; U.S. Patent Application Publication No. 2015/0018633, Jan. 15, 2015.
m. International Patent Application No. PCT/US2012/043910 entitled "Unified Platform For Monitoring and Control of Blood Glucose Levels in Diabetic Patients", filed Jun. 23, 2012; International Patent Application Publication No. WO 2012/178134, Dec. 27, 2012.
n. U.S. patent application Ser. No. 14/128,811 entitled "Methods and Apparatus for Modular Power Management and Protection of Critical Services in Ambulatory Medical Devices", filed Dec. 23, 2013; U.S. Patent Application Publication No. 2014/0215239, Jul. 31, 2014.
o. International Patent Application No. PCT/US2012/043883 entitled "Methods and Apparatus for Modular Power Management and Protection of Critical Services in Ambulatory Medical Devices", filed Jun. 22, 2012; International Patent Application Publication No. WO 2012/178113, Dec. 27, 2012.
p. U.S. patent application Ser. No. 14/015,831 entitled "CGM-Based Prevention of Hypoglycemia Via Hypoglycemia Risk Assessment and Smooth Reduction Insulin Delivery", filed Aug. 30, 2013.
q. U.S. patent application Ser. No. 13/203,469 entitled "CGM-Based Prevention of Hypoglycemia via Hypoglycemia Risk Assessment and Smooth Reduction Insulin Delivery", filed Aug. 25, 2011; U.S. Pat. No. 8,562,587, issued Oct. 22, 2013.
r. International Patent Application No. PCT/US2010/025405 entitled "CGM-Based Prevention of Hypoglycemia via Hypoglycemia Risk Assessment and Smooth Reduction Insulin Delivery", filed Feb. 25, 2010; International Patent Application Publication No. WO 2010/099313, Sep. 2, 2010.
s. International Patent Application No. PCT/US2013/042745 entitled "Insulin-Pramlintide Compositions and Methods for Making and Using Them", filed May 24, 2013; International Application Publication No. WO 2013/177565, Nov. 28, 2013.
t. U.S. patent application Ser. No. 13/637,359 entitled "Method, System, and Computer Program Product for Improving the Accuracy of Glucose Sensors Using Insulin Delivery Observation in Diabetes", filed Sep. 25, 2012; U.S. Patent Application Publication No. 2013/0079613, Mar. 28, 2013.
u. International Patent Application No. PCT/US2011/029793 entitled "Method, System, and Computer Program Product for Improving the Accuracy of Glucose Sensors Using Insulin Delivery Observation in Diabetes", filed Mar. 24, 2011; International Patent Application Publication No. WO 2011/119832, Sep. 29, 2011.
v. U.S. patent application Ser. No. 13/634,040 entitled "Method and System for the Safety, Analysis, and Supervision of Insulin Pump Action and Other Modes of Insulin Delivery in Diabetes", filed Sep. 11, 2012; U.S. Patent Application Publication No. 2013/0116649, May 9, 2013.
w. International Patent Application No. PCT/US2011/028163 entitled "Method and System for the Safety, Analysis, and Supervision of Insulin Pump Action and Other Modes of Insulin Delivery in Diabetes", filed Mar. 11, 2011; International Patent Application Publication No. WO 2011/112974, Sep. 15, 2011.
x. U.S. patent application Ser. No. 13/394,091 entitled "Tracking the Probability for Imminent Hypoglycemia in Diabetes from Self-Monitoring Blood Glucose (SMBG) Data", filed Mar. 2, 2012; U.S. Patent Application Publication No. 2012/0191361, Jul. 26, 2012.
y. International Patent Application No. PCT/US2010/047711 entitled "Tracking the Probability for Imminent Hypoglycemia in Diabetes from Self-Monitoring Blood Glucose (SMBG) Data", filed Sep. 2, 2010; International Patent Application Publication No. WO 2011/028925, Mar. 10, 2011.
z. U.S. patent application Ser. No. 13/393,647 entitled "System, Method and Computer Program Product for Adjustment of Insulin Delivery (AID) in Diabetes Using Nominal Open-Loop Profiles", filed Mar. 1, 2012; U.S. Patent Application Publication No. 2012/0245556, Sep. 27, 2012.
aa. International Patent Application No. PCT/US2010/047386 entitled "System, Method and Computer Program Product for Adjustment of Insulin Delivery (AID) in Diabetes Using Nominal Open-Loop Profiles", filed Aug. 31, 2010; International Application Publication No. WO 2011/028731, Mar. 10, 2011.
bb. U.S. patent application Ser. No. 13/380,839 entitled "System, Method, and Computer Simulation Environment for In Silico Trials in Pre-Diabetes and Type 2 Diabetes", filed Dec. 25, 2011; U.S. Patent Application Publication No. 2012/0130698, May 24, 2012.
cc. International Patent Application No. PCT/US2010/040097 entitled "System, Method, and Computer Simulation Environment for In Silico Trials in Prediabetes and Type 2 Diabetes", filed Jun. 25, 2010; International Application Publication No. WO 2010/151834, Dec. 29, 2010.

dd. U.S. patent application Ser. No. 13/322,943 entitled "System Coordinator and Modular Architecture for Open-Loop and Closed-Loop Control of Diabetes", filed Nov. 29, 2011; U.S. Patent Application Publication No. 2012/0078067, Mar. 29, 2012.

ee. International Patent Application No. PCT/US2010/036629 entitled "System Coordinator and Modular Architecture for Open-Loop and Closed-Loop Control of Diabetes", filed May 28, 2010; International Patent Application Publication No. WO 2010/138848, Dec. 2, 2010.

ff. U.S. patent application Ser. No. 13/131,467 entitled "Method, System, and Computer Program Product for Tracking of Blood Glucose Variability in Diabetes", filed May 26, 2011; U.S. Patent Application Publication No. 2011/0264378, Oct. 27, 2011.

gg. International Patent Application No. PCT/US2009/065725 entitled "Method, System, and Computer Program Product for Tracking of Blood Glucose Variability in Diabetes", filed Nov. 24, 2009; International Patent Application Publication No. WO 2010/062898, Jun. 3, 2010.

hh. U.S. patent application Ser. No. 12/975,580 entitled "Method, System, and Computer Program Product for the Evaluation of Glycemic Control in Diabetes from Self-Monitoring Data", filed Dec. 22, 2010; U.S. Patent Application Publication No. 2012/0004512, Jan. 5, 2012.

ii. U.S. patent application Ser. No. 11/305,946 entitled "Method, System, and Computer Program Product for the Evaluation of Glycemic Control in Diabetes from Self-Monitoring Data", filed Dec. 19, 2005; U.S. Pat. No. 7,874,985, issued Jan. 25, 2011.

jj. U.S. patent application Ser. No. 10/240,228 entitled "Method, System, and Computer Program Product for the Evaluation of Glycemic Control in Diabetes from Self-Monitoring Data", filed Sep. 26, 2002; U.S. Pat. No. 7,025,425, issued Apr. 11, 2006.

kk. International Patent Application No. PCT/US2001/009884 entitled "Method, System, and Computer Program Product for the Evaluation of Glycemic Control in Diabetes", filed Mar. 29, 2001; International Application Publication No. WO 2001/72208, Oct. 4, 2001.

ll. U.S. patent application Ser. No. 12/674,348 entitled "Method, Computer Program Product and System for Individual Assessment of Alcohol Sensitivity", filed Feb. 19, 2010; U.S. Patent Application Publication No. 2011/0264374, Oct. 27, 2011.

mm. International Patent Application No. PCT/US2008/073738 entitled "Method, Computer Program Product and System for Individual Assessment of Alcohol Sensitivity", filed Aug. 20, 2008; International Patent Application Publication No. WO 2009/026381, Feb. 26, 2009.

nn. U.S. patent application Ser. No. 12/665,149 entitled "Method, System and Computer Program Product for Evaluation of Insulin Sensitivity, Insulin/Carbohydrate Ratio, and Insulin Correction Factors in Diabetes from Self-Monitoring Data", filed Dec. 17, 2009; U.S. Patent Application Publication No. 2010/0198520, Aug. 5, 2010.

oo. International Patent Application No. PCT/US2008/069416 entitled "Method, System and Computer Program Product for Evaluation of Insulin Sensitivity, Insulin/Carbohydrate Ratio, and Insulin Correction Factors in Diabetes from Self-Monitoring Data", filed Jul. 8, 2008; International Patent Application Publication No. WO 2009/009528, Jan. 15, 2009.

pp. U.S. patent application Ser. No. 12/664,444 entitled "Method, System and Computer Simulation Environment for Testing of Monitoring and Control Strategies in Diabetes", filed Dec. 14, 2009; U.S. Patent Application Publication No. 2010/0179768, Jul. 15, 2010.

qq. International Patent Application No. PCT/US2008/067725 entitled "Method, System and Computer Simulation Environment for Testing of Monitoring and Control Strategies in Diabetes", filed Jun. 20, 2008; International Patent Application Publication No. WO 2008/157781, Dec. 24, 2008.

rr. U.S. patent application Ser. No. 12/516,044 entitled "Method, System, and Computer Program Product for the Detection of Physical Activity by Changes in Heart Rate, Assessment of Fast Changing Metabolic States, and Applications of Closed and Open Control Loop in Diabetes", filed May 22, 2009; U.S. Pat. No. 8,585,593, issued Nov. 19, 2013.

ss. International Patent Application No. PCT/US2007/085588 entitled "Method, System, and Computer Program Product for the Detection of Physical Activity by Changes in Heart Rate, Assessment of Fast Changing Metabolic States, and Applications of Closed and Open Control Loop in Diabetes", filed Nov. 27, 2007; International Patent Application Publication No. WO2008/067284, Jun. 5, 2008.

tt. U.S. patent application Ser. No. 12/159,891 entitled "Method, System and Computer Program Product for Evaluation of Blood Glucose Variability in Diabetes from Self-Monitoring Data", filed Jul. 2, 2008; U.S. Patent Application Publication 2009/0171589, Jul. 2, 2009.

uu. International Patent Application No. PCT/US2007/000370 entitled "Method, System and Computer Program Product for Evaluation of Blood Glucose Variability in Diabetes from Self-Monitoring Data", filed Jan. 5, 2007; International Application Publication No. WO 2007/081853, Jul. 19, 2007.

vv. U.S. patent application Ser. No. 12/065,257 entitled "Accuracy of Continuous Glucose Sensors", filed Feb. 28, 2008; U.S. Patent Application Publication No. 2008/0314395, Dec. 25, 2008.

ww. International Patent Application No. PCT/US2006/033724 entitled "Method for Improvising Accuracy of Continuous Glucose Sensors and a Continuous Glucose Sensor Using the Same", filed Aug. 29, 2006; International Application Publication No. WO 2007027691, Mar. 8, 2007.

xx. U.S. patent application Ser. No. 11/943,226 entitled "Systems, Methods and Computer Program Codes for Recognition of Patterns of Hyperglycemia and Hypoglycemia, Increased Glucose Variability, and Ineffective Self-Monitoring in Diabetes", filed Nov. 20, 2007; U.S. Patent Application Publication No. 2008/0154513, Jun. 26, 2008.

yy. U.S. patent application Ser. No. 11/578,831 entitled "Method, System and Computer Program Product for Evaluating the Accuracy of Blood Glucose Monitoring Sensors/Devices", filed Oct. 18, 2006; U.S. Pat. No. 7,815,569, issued Oct. 19, 2010.

zz. International Patent Application No. US2005/013792 entitled "Method, System and Computer Program Product for Evaluating the Accuracy of Blood Glucose Monitoring Sensors/Devices", filed Apr. 21, 2005; International Application Publication No. WO 2005/106017, Nov. 10, 2005.

aaa. U.S. patent application Ser. No. 10/592,883 entitled "Method, Apparatus, and Computer Program Product for Stochastic Psycho-physiological Assessment of Attentional Impairments", filed Sep. 15, 2006; U.S. Pat. No. 7,761,144, issued Jul. 20, 2010.

bbb. U.S. patent application Ser. No. 10/524,094 entitled "Method, System, And Computer Program Product For The Processing Of Self-Monitoring Blood Glucose (SMBG) Data To Enhance Diabetic Self-Management", filed Feb. 9, 2005; U.S. Pat. No. 8,538,703, issued Sep. 17, 2013.

ccc. International Patent Application No. PCT/US2003/025053 entitled "Managing and Processing Self-Monitoring Blood Glucose", filed Aug. 8, 2003; International Application Publication No. WO 2001/72208, Oct. 4, 2001.

ddd. International Patent Application No. PCT/US2002/005676 entitled "Method and Apparatus for the Early Diagnosis of Subacute, Potentially Catastrophic Illness", filed Feb. 27, 2002; International Application Publication No. WO 2002/67776, Sep. 6, 2002.

eee. U.S. patent application Ser. No. 09/793,653 entitled "Method and Apparatus for the Early Diagnosis of Subacute, Potentially Catastrophic Illness", filed Feb. 27, 2001; U.S. Pat. No. 6,804,551, issued Oct. 12, 2004.

fff. U.S. patent application Ser. No. 10/069,674 entitled "Method and Apparatus for Predicting the Risk of Hypoglycemia", filed Feb. 22, 2002; U.S. Pat. No. 6,923,763, issued Aug. 2, 2005.

ggg. International Patent Application No. PCT/US00/22886 entitled "METHOD AND APPARATUS FOR PREDICTING THE RISK OF HYPOGLYCEMIA", filed Aug. 21, 2000; International Application Publication No. WO 2001/13786, Mar. 1, 2001.

hhh. U.S. patent application Ser. No. 12/665,420 entitled "LQG Artificial Pancreas Control System and Related Method", filed Dec. 18, 2009; U.S. Patent Application Publication No. 2010/0249561, Sep. 30, 2010.

iii. International Patent Application No. PCT/US2008/067723 entitled "LQG Artificial Pancreas Control System and Related Method", filed Jun. 20, 2008; International Patent Application Publication No. WO 2008/157780, Dec. 24, 2008.

In summary, while the present invention has been described with respect to specific embodiments, many modifications, variations, alterations, substitutions, and equivalents will be apparent to those skilled in the art. The present invention is not to be limited in scope by the specific embodiment described herein. Indeed, various modifications of the present invention, in addition to those described herein, will be apparent to those of skill in the art from the foregoing description and accompanying drawings. Accordingly, the invention is to be considered as limited only by the spirit and scope of the disclosure, including all modifications and equivalents.

Still other embodiments will become readily apparent to those skilled in this art from reading the above-recited detailed description and drawings of certain exemplary embodiments. It should be understood that numerous variations, modifications, and additional embodiments are possible, and accordingly, all such variations, modifications, and embodiments are to be regarded as being within the spirit and scope of this application. For example, regardless of the content of any portion (e.g., title, field, background, summary, abstract, drawing figure, etc.) of this application, unless clearly specified to the contrary, there is no requirement for the inclusion in any claim herein or of any application claiming priority hereto of any particular described or illustrated activity or element, any particular sequence of such activities, or any particular interrelationship of such elements. Moreover, any activity can be repeated, any activity can be performed by multiple entities, and/or any element can be duplicated. Further, any activity or element can be excluded, the sequence of activities can vary, and/or the interrelationship of elements can vary. Unless clearly specified to the contrary, there is no requirement for any particular described or illustrated activity or element, any particular sequence or such activities, any particular size, speed, material, dimension or frequency, or any particularly interrelationship of such elements. Accordingly, the descriptions and drawings are to be regarded as illustrative in nature, and not as restrictive. Moreover, when any number or range is described herein, unless clearly stated otherwise, that number or range is approximate. When any range is described herein, unless clearly stated otherwise, that range includes all values therein and all sub ranges therein. Any information in any material (e.g., a United States/foreign patent, United States/foreign patent application, book, article, etc.) that has been incorporated by reference herein, is only incorporated by reference to the extent that no conflict exists between such information and the other statements and drawings set forth herein. In the event of such conflict, including a conflict that would render invalid any claim herein or seeking priority hereto, then any such conflicting information in such incorporated by reference material is specifically not incorporated by reference herein.

What is claimed is:

1. A method for assessing actionable glycemic risk comprising:

obtaining an output continuous glucose monitoring (BG) signal at a time t;

determining a glycemic cost signal at the time t based on the output continuous glucose monitoring BGsignal with a glycemic cost function algorithm that attributes equal cost to each of two end points (BGtarget,lo, BGtarget,hi) of a desired blood glucose target range;

using the glycemic cost signal to quantify actionable risk and unaddressable risk by determining an instantaneous hypoglycemia risk at the time t and an instantaneous hyperglycemia risk at the time t based on the glycemic cost signal, wherein actionable risk includes actionable hypoglycemia risk and actionable hyperglycemia risk;

averaging each of the instantaneous hypoglycemia risk and the instantaneous hyperglycemia risk over a defined interval to determine a moving average hypoglycemia risk and a moving average hyperglycemia risk;

averaging each of the moving average hypoglycemia risk and the moving average hyperglycemia risk across multiple days to generate a hypoglycemia risk profile (lop(s)) and a hyperglycemia risk profile (hip(s)) at time s of the day;

administering insulin to a patient, via an insulin device, based on the generated hypoglycemia risk profile (lop(s)) and hyperglycemia risk profile (hip(s)).

2. The method of claim 1, wherein the glycemic cost function algorithm is:

$$J(BG) = c\left[\ln\left(\frac{BG}{\sqrt{BG_{target,lo} \cdot BG_{target,hi}}}\right)\right]^2,$$

where c is a constant and BG is a blood glucose value.

3. The method of claim 1, wherein the instantaneous hypoglycemia risk and the instantaneous hyperglycemia risk are determined by the algorithm:

rlo(BG)=J(BG), if BG<sqrt(BGtarget,lo*BGtarget,hi) 0, otherwise rhi(BG)=J(BG), if BG>=sqrt(BGtarget,lo*BGtarget,hi) 0, otherwise, wherein J(BG) is the glycemic cost function, rlo(BG) is the instantaneous hypoglycemia risk and rhi(BG) is the instantaneous hyperglycemia risk.

4. The method of claim 1, comprising:
discounting the instantaneous hypoglycemia risk or the instantaneous hyperglycemia risk if the slope of the BG signal indicates that the BG signal is trending towards a midpoint of the blood glucose target range.

5. The method of claim 1, comprising:
summing the hypoglycemia risk profile and the hyperglycemia risk profile to generate a total risk profile (trp).

6. The method of claim 5, comprising:
using the hypoglycemia risk profile to generate an actionable hypoglycemia risk; and
using the hyperglycemia risk profile to generate an actionable hyperglycemia risk.

7. The method of claim 6, wherein the actionable hypoglycemia risk is generated by the algorithm ARlow(s)=lop(s)*[lop(s)−hip(s)]$^+$/trp(s), and the actionable hyperglycemia risk is generated by the algorithm ARhigh(s)=hip(s)*[hip(s)−lop(s)]$^+$/trp(s).

8. The method of claim 7, wherein the unaddressable risk is generated by the algorithm:

UR(s)=[trp(s)−ARlow(s)−ARhigh(s)]/2.

9. The method of claim 1, comprising:
interpolating the BG signal to fill gaps in the BG signal.

10. The method of claim 1, comprising:
using the BG signal only for real-time determination of actionable risk and unaddressable risk.

11. The method of claim 1, comprising:
using the BG signal for retrospective analysis of actionable risk and unaddressable risk.

12. A system for assessing actionable glycemic risk comprising:
a digital processor;
a continuous blood glucose monitoring (BG) sensor in communication with the digital processor, the continuous blood glucose monitoring (BG) sensor being configured to generate a blood glucose signal;
a risk determination module, configured to:
receive the glucose signal from the continuous glucose monitoring sensor, and generate an actionable hypoglycemia risk signal, an actionable hyperglycemia risk signal, and an unaddressable risk signal using a glycemic cost function algorithm that attributes equal cost to each of two end points (BGtarget,lo, BGtarget,hi) of a desired blood glucose target range,
determine an instantaneous hypoglycemia risk at the time t and an instantaneous hyperglycemia risk at the time t based on the risk signals,
average each of the instantaneous hypoglycemia risk and the instantaneous hyperglycemia risk over a defined interval to determine a moving average hypoglycemia risk and a moving average hyperglycemia risk;
average each of the moving average hypoglycemia risk and the moving average hyperglycemia risk across multiple days to generate a hypoglycemia risk profile (lop(s)) and a hyperglycemia risk profile (hip(s)) at time s of the day; and
an insulin device that administers insulin to a patient based on the generated hypoglycemia risk profile (lop(s)) and hyperglycemia risk profile (hip(s)).

13. The system of claim 12, wherein the glycemic cost function algorithm is:

$$J(BG) = c\left[\ln\left(\frac{BG}{\sqrt{BG_{target,lo} \cdot BG_{target,hi}}}\right)\right]^2,$$

where c is a constant and BG is a blood glucose value.

14. The system of claim 12, wherein the risk determination module is configured to:
discount the instantaneous hypoglycemia risk or the instantaneous hyperglycemia risk when the slope of the BG signal indicates that the BG signal is trending towards a midpoint of the blood glucose target range.

15. The system of claim 12, wherein the risk determination module is configured to:
sum the hypoglycemia risk profile and the hyperglycemia risk profile to generate a total risk profile (trp).

16. The system of claim 15, wherein the risk determination module is configured to:
a. generate an actionable hypoglycemia risk signal based on the hypoglycemia risk profile by an algorithm ARlow(s)=lop(s)*[lop(s)−hip(s)]$^+$/trp(s);
b. generate an actionable hyperglycemia risk signal based on the hyperglycemia risk profile by an algorithm ARhigh(s)=hip(s)*[hip(s)−lop(s)] $^+$/trp(s); and
c. generate an unaddressable risk signal by an algorithm UR(s)=[trp(s)−ARlow(s)−ARhigh(s)]/2.

17. The system of claim 12, comprising:
an insulin pump in communication with the digital processor and configured to dispense insulin in response to real-time analysis of at least one of the actionable hypoglycemia risk signal, the actionable hyperglycemia risk signal, and the unaddressable risk signal.

* * * * *